United States Patent [19]

Jenkins et al.

[11] Patent Number: 5,026,914

[45] Date of Patent: * Jun. 25, 1991

[54] HYDROGENATION OF AROMATIC AMINES USING RHODIUM ON TITANIA OR ZIRCONIA SUPPORT

[75] Inventors: Richard J. Jenkins, Coopersburg; Robert A. Treskot, Walnutport; Gamini A. Vedage, Bethlehem; James F. White, Macungie, all of Pa.

[73] Assignee: Air Products and Chemicals, Inc., Allentown, Pa.

[*] Notice: The portion of the term of this patent subsequent to Oct. 2, 2004 has been disclaimed.

[21] Appl. No.: 336,184

[22] Filed: Apr. 11, 1989

[51] Int. Cl.$^5$ ............................................. C07C 209/72
[52] U.S. Cl. ................................... 564/451; 564/450
[58] Field of Search ................. 564/450, 451; 502/261

[56] References Cited

U.S. PATENT DOCUMENTS

| | | | |
|---|---|---|---|
| 2,079,404 | 5/1937 | Harris | 23/233 |
| 2,511,028 | 6/1950 | Whitman | 260/563 |
| 2,606,924 | 8/1952 | Whitman | 260/563 |
| 2,606,925 | 8/1952 | Whitman | 260/563 |
| 2,606,928 | 8/1952 | Barkdoll et al. | 260/563 |
| 3,591,635 | 7/1971 | Farrissey, Jr. | 260/563 B |
| 3,636,108 | 1/1972 | Brake | 260/563 D |
| 3,644,522 | 2/1972 | Brake | 260/563 D |
| 3,697,449 | 10/1972 | Brake | 252/474 |
| 3,856,862 | 12/1974 | Chung et al. | 260/563 B |
| 4,218,308 | 8/1980 | Itoh et al. | 208/143 |
| 4,376,724 | 3/1983 | Mita et al. | 252/460 |
| 4,459,372 | 7/1984 | Arena | 502/351 |
| 4,754,070 | 6/1988 | Casey et al. | 564/451 |

FOREIGN PATENT DOCUMENTS 2630562  1/1978  Fed. Rep. of Germany .

*Primary Examiner*—Richard L. Raymond
*Assistant Examiner*—Peter G. O'Sullivan
*Attorney, Agent, or Firm*—Russell L. Brewer; James C. Simmons; William F. Marsh

[57] ABSTRACT

This invention relates to an improved hydrogenation process wherein aromatic amines are hydrogenated to their ring hydrogenated counterparts using an improved rhodium catalyst and to the catalyst. The aromatic amines are represented by the formulas:

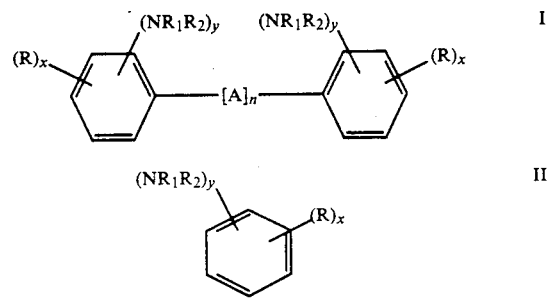

wherein R is hydrogen or $C_{1-6}$ aliphatic, $R_1$ and $R_2$ are hydrogen or $C_{1-6}$ aliphatic, A is $C_{1-4}$ alkylene, NH, or

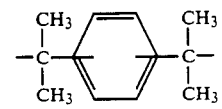

n is 0-2, x is 1-3 and y is 1 to 2 except the sum of the y groups in Formula I excluding A may be 1.

The rhodium catalyst is supported on titania bonded to silica or zirconia or bonded with silica, zirconia or titania from a sol or zirconia bonded with silica or alumina. The resulting catalyst has greater activity and attrition resistance. Zirconia bonded with silica or alumina also results in a catalyst with increased attrition resistance.

27 Claims, No Drawings

HYDROGENATION OF AROMATIC AMINES USING RHODIUM ON TITANIA OR ZIRCONIA SUPPORT

TECHNICAL FIELD

This invention pertains to a process for hydrogenating aromatic amines using a rhodium catalyst and to the catalyst itself.

BACKGROUND OF THE INVENTION

There is substantial literature in the art with respect to the hydrogenation of aromatic amines, e.g., methylenedianiline to produce 4,4'-methylenedi(cyclohexylamine), also called bis(para-aminocyclohexyl)methane, and bis(4-aminocyclohexyl)methane hereinafter often referred to as PACM.

Some of the early hydrogenation work to produce PACM was done by Whitman and Barkdoll, et al. and their work is set forth in a series of U.S. Pat. Nos. e.g., 2,511,028; 2,606,924; 2,606,925; and 2,606,928. Basically the processes described in these patents involve the hydrogenation of methylenedianiline at pressures in excess of 200 psig, preferably in excess of 1,000 psig, at temperatures within a range of 80° to 275° C. utilizing a ruthenium catalyst for the hydrogenation. The hydrogenation is carried out under liquid phase conditions by using an inert organic solvent in the hydrogenation process. Examples of ruthenium catalysts utilized for the hydrogenation process include ruthenium oxides such as ruthenium sesquioxide and ruthenium dioxide.

Brake, et al. continued in the development of processes for manufacturing PACM by hydrogenating methylenedianiline. They found that if the ruthenium was carried upon a support and the support was alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation. Representative patents showing the utilization of alkali moderated ruthenium catalysts to hydrogenate methylenedianiline include U.S. Pat. Nos. 3,636,108; 3,644,522; and 3,697,449. Alkali metal and alkaline earth metal nitrates and sulfates have similarly been shown effective in U.S. Pat. No. 4,448,995 under high pressure (4000 psia) hydrogenation conditions. Representative supports in the '449 patent include bauxite, periclase, zirconia, titania, diatomaceous earth, etc.

Other catalysts have been utilized for the hydrogenation of methylenedianiline and examples are shown in U.S. Pat. Nos. 3,591,635 and 3,856,862. Both disclose the use of a rhodium component as a catalytic material and each require the use of an aliphatic alcohol as a solvent. The rhodium is alkali moderated using ammonium hydroxide as a pretreatment or by carrying out the reaction in the presence of ammonia. European application 66,212 discloses the use of rhodium on alumina to obtain 15–40% trans, transisomer ratio but again the pressures are high (4000 psia).

U.S. Pat. No. 4,376,724 discloses a catalyst with rhodium present in the surface layer of particles of silica or titania which is alleged as being suited for the synthesis of oxygen containing compounds and various hydrogenation reactions including the nuclear hydrogenation of aromatic compounds and in the hydrogenation of unsaturated bonds of olefins, nitriles, etc. The catalyst is prepared by dipping the support into an aqueous solution of a water soluble rhodium salt adjusted to a specific pH followed by drying and reduction. The supports include silica or titania as a single component, mixtures of silica or titania and with compound oxides containing as the main constituent, silica or titania, such compound oxides, including alumina, magnesia, thoria or zirconia.

U.S. Pat. No. 4,218,308 discloses a catalyst for the hydrogenation of hydrocarbon oils which comprise a silica/alumina carrier having a silica content of less than 40% by weight and at least one Group VIII noble metal with palladium, platinum and rhodium being candidates.

U.S. Pat. No. 4,233,183 broadly discloses a plate-shaped catalyst prepared from a slurry of hydrated titania and a sol selected from the group consisting of silica sol, alumina sol, or titania sol. A catalytically active component is deposited upon the carrier. Suggested examples of catalytically active components include chromium, manganese, and noble metals such as platinum, rhodium, and palladium.

U.S. Pat. No. 4,547,557 discloses a silica-titania cogel as a support for a chromium catalyst in the preparation of polyethylene. It is produced in a two-step process wherein in the first step an alkali polysilicate is partially hydrolyzed in an alkaline organic solvent and thereafter a tetralkyl titanate added with an excess of water to complete the hydrolysis. The chromium compound is deposited on the surface of the silica-titania cogel or is co-precipitated in the form of the cogel to produce the catalyst.

U.S. Pat. No. 2,079,404 discloses a method of preparing a catalyst incorporating a platinum metal such as platinum, palladium, or rhodium on a vitreous silica support.

SUMMARY OF THE INVENTION

This invention relates to an improved catalyst and catalytic process for producing aromatic amines such as 4,4'-methylenedi(cyclohexylamine) (PACM) by the catalytic hydrogenation of such aromatic amines to produce their hydrogenated counterparts. The improvement in the hydrogenation process comprises using a catalytic system comprising rhodium supported on a titania support bonded with silica or zirconia or with silica, zirconia or titania through a sol or zirconia bonded with silica or alumina. Preferably the catalyst comprises rhodium and ruthenium wherein the light ratio of rhodium to ruthenium, calculated on metal content, is from 1 to 12:1. In addition, the invention pertains to the catalyst.

There are several advantages associated with this process and catalyst. These include:

an ability to utilize an impure or crude nondistilled aromatic amine such as bridged dianillines, i.e. one containing oligomers and the formamide derivative of a dianiline as a reactant and yet obtain a hydrogenated product in high selectivity whereas conventional rhodium catalysts have been inactive in hydrogenating crude methylene bridged aromatics;

an ability to eliminate alkali-moderation of the rhodium catalyst to produce the ring hydrogenated counterpart in high conversion and with excellent reaction rates;

an ability to use the catalyst for continued periods of time with only modest maintenance or regeneration; and a catalyst having excellent attrition resistance in liquid phase hydrogenation reactions.

DETAILED DESCRIPTION OF THE INVENTION

This invention relates to an improvement in the conventional ring hydrogenation of aromatic amines and to the catalysts and these amines are represented by the formulas:

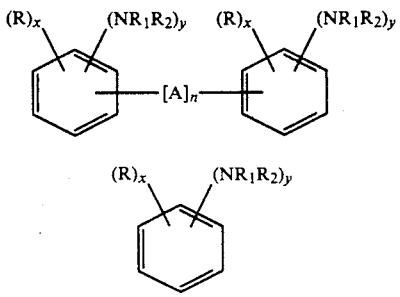

wherein R is hydrogen or $C_{1-6}$ aliphatic, $R_1$ is hydrogen, or $C_{1-6}$ aliphatic, A is $C_{1-4}$ alkylene, NH, or

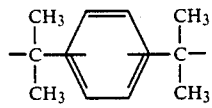

n is 0-2, x is 1-3 and y is 1-2 except the sum of the y groups in Formula I excluding A may be 1. Where R is hydrogen then the ring is unsubstituted. By the practice of this invention, one is able to selectively produce a ring hydrogenated reaction product in high selectively with excellent reaction rates.

The aromatic amines useful in the practice of the process can be bridged polynuclear aromatic amines or mononuclear aromatic amines. These can be substituted with various substituents such as aliphatic groups containing from 1-6 carbon atoms. Further, the amine group can be substituted with aliphatic groups such as alkyl or alkanol groups resulting in secondary and tertiary amine substituents. Examples of bridged aromatic amines include methylenedianilines such as bis(para-aminophenyl) methane and bis(para-amino-2-methylphenyl) methane; toluidine; bis(diaminophenyl)methane; α,α'-bis(4-aminophenyl-para-diisopropyl benzene(bisaniline P), bis(diaminophenyl)propane (bisaniline A); N-$C_{1-4}$-aliphatic derivatives and N,N'$C_{1-4}$ aliphatic secondary and tertiary amine derivatives of the above bridged aromatic amines. Examples of mononuclear aromatic amines include 2,4- and 2,6-toluenediamine, aniline, butenyl-aniline derivatives, 1-methyl-3,5-diethyl-2,4- and 2,6-diaminobenzene (diethyltoluenediamine); monoisopropyltoluenediamine, cyclopentyltoluenediamine, ortho-tolidine, ethyl toluidine, xylenediamine, mesitylenediamine, phenylenediamine and the N and N,N'$C_{1-4}$ aliphatic secondary and tertiary amine derivatives of the mononuclear aromatic monoamines and mononuclear aromatic diamines.

As with conventional processes the hydrogenation process usually is carried out under liquid phase conditions, such liquid phase conditions being maintained typically by carrying out the hydrogenation in the presence of a solvent. Although as reported in the art, it is possible to effect reaction in the absence of a solvent, the processing usually is much simpler when a solvent is employed. Representative solvents suited for hydrogenation of aromatic amines include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred. Although in some processes water can be used as a cosolvent, it is preferred that the system be maintained in an anhydrous state or at least maintained so that the water concentration is less than 0.5% by weight. Water, when present in the system, tends to increase the amount of by-product alcohols and heavy condensation products during the hydrogenation process and tends to deactivate the catalyst system.

When a solvent is used, it can be used in concentrations as low as 50% by weight based upon the aromatic amine introduced into the reaction and typically the solvent is used at levels from about 75 to about 200% by weight of the starting compound. Under some circumstances solvent amounts as high as 1000 to 2000% based upon the weight of aromatic amine and used.

In contrast to the prior art hydrogenation processes, particularly for bridged anilines, hydrogen partial pressures can range from about 200 to 4000 psig, preferably no higher than 2500 psig and typically can be as low as from about 700 to 1500 psig, which may be preferred for lower equipment and operating costs. When the pressure is raised toward the upper end of the operating range, higher reaction rates may be achieved.

The ability to ring hydrogenate aromatic amines, and particularly methylenedianiline at low hydrogen partial pressures and obtain high conversion with excellent reaction rates while maintaining loss to attrition, is achieved by the utilization of a specific catalyst system. The catalyst utilized in the hydrogenation process comprises rhodium supported on a titania, or chemically bonded with silica, or with titania or silica through sol or rhodium on a support of zirconia on silica or alumina and in a preferred embodiment a mixture of rhodium and ruthenium carried on the titania support. However, the ruthenium component may be combined with the rhodium or present as a physical admixture carried on a support, e.g., alumina or titania. The support is one wherein titania is bonded to silica or silica or titania through a sol or zirconia or bonded to titania through a sol. This is in contrast to catalyst systems wherein the supports are admixed as physical mixtures.

Preparation of the support where titania is bonded to silica involves contacting the titania powder with a silica sol. The combination of silica sol with titania results in a bonding, perhaps chemical, which is stronger than that associated with a physical mixture.

The support which provides for enhanced attrition resistance and enhanced activity, particularly where a titania or silica sol is combined with the titania support, is prepared by contacting titanium dioxide having a particle size typically from 15 to 40 nanometers with a preselected sol. A sol is one which contains colloidally dispersed silica, or titania in water. The concentration of silica or titania in the sol usually ranges from about 12 to 40 percent parts by weight of titania or silica. This mixture is stirred with the titania dioxide in an amount to provide from about 10 to 60 weight parts silica or titania per 100 weight parts titania dioxide and then dried. A mixed oxide support may be prepared by containing solutions of a zirconium salt, e.g., zirconia nitrate and ether sodium silicate of sodium aluminate. This is followed by filtering, washing, drying.

The resulting dried mass then is ground to produce particulate titania support particles of predetermined particle size, e.g., a −40 to +100 U.S. mesh standard sieve. The support is contacted with the water-soluble rhodium salt and impregnated with such salt. The impregnated support is recovered, dried, and the rhodium metal reduced. If it is desired that a ruthenium component is present in the catalyst, a water-soluble ruthenium salt may be combined with the water-soluble rhodium salt and impregnated into the titania-silica or titania-titania sol. Another support variation is the zirconia-silica or zirconia-alumina support where the zirconia is bonded with the silica or alumina.

The rhodium salt is combined with the titania support bonded to the silica, titania from the sol or the mixed oxide, in an amount based upon its weight as metal, to provide a ratio of about 1 to 25 weight parts rhodium per 100 weight parts of support, preferably 3 to 8 weight parts rhodium per 100 weight parts support. With respect to the preferred catalyst, the rhodium to ruthenium weight ratio is from about 1–12:1, preferably 4–8 weight parts rhodium/weight part ruthenium on the support.

In the past, to maintain high activity of the catalyst system in the hydrogenation process it was proposed that the rhodium and ruthenium component, if present, be alkali moderated. Alkali moderation techniques to produce the catalyst system are well known and the techniques disclosed in U.S. Pat. No. 3,636,108 for the alkali moderation of ruthenium can be utilized for the production of rhodium. Such method is incorporated by reference. However, as previously noted, the titania or mixed oxide support apparently does not need significant alkali metal hydroxide moderation as do other supports, e.g., alumina. Typically, such alkali moderation involves the treatment of the catalyst and support material with an alkali metal hydroxide such as, sodium, lithium or potassium hydroxide or alkali metal alkoxide such as sodium, lithium, or potassium methoxide or ethoxide in an amount to provide from 0.1 to 15% by weight of a basic metal compound calculated as alkali metal. Often, alkali moderation of the catalyst is done prior to reduction of the catalyst with aqueous dilute alkali metal hydroxide during or following metal deposition on the chosen support. Alkali moderation can also be accomplished, in situ, i.e., during hydrogenation by adding alkali metal hydroxide, e.g., lithium hydroxide, alkali metal alkoxide or by the addition of ammonia to the reaction medium.

As a possible explanation for the enhanced catalytic effect of the rhodium catalyst in the titania support bonded with the silica, titania sol or the mixed oxide, it is believed the resulting pore structure first enhances the presentation of the rhodium during reaction. Second, the reduced attrition due to enhanced strength minimizes plugging of the catalyst surface with fines.

The following examples are intended to illustrate various embodiments of the invention and all parts and percentages given are weight parts or weight percents unless otherwise specified.

EXAMPLE 1

Catalyst Preparation Rhodium on Titania-Silica Sol Support a. 201 grams of titanium dioxide powder, e.g., Degussa P-25, having an average primary particle size of 15–40 nanometers and <1.5% moisture was added to a sigma blade batch mixer. To the powder was added a silica sol, e.g., Nalco 2327 colloidal silica, which contains approximately 40% by weight silica. A total of 293 grams of the silica sol was added to the titanium dioxide powder while mixing to provide about 37% by weight silica based on the weight of the support. Mixing was completed in approximately 5 minutes or when a lumpy paste-like product was formed. This material was scraped from the mixer, placed into a drying tray and dried in a drying oven at 260° C. overnight. During the drying process there was approximately a 35% moisture loss. The dried lumps were then ground to −40+100 mesh particle size. In this case, two pieces of grinding equipment were used: a 2 inch plate grinder, which broke up the larger lumps of titania-silica support and a Thomas-Wiley Intermediate Mill, with a 20 mesh screen installed. The grinding step was continued until all of the material passed through the 40 mesh screen. Only the particles which passed through the 40 mesh screen and stayed on the 100 mesh screen were saved and used as the support. The grinding recovery was 70–80%.

b. A second sample was also made in the same manner with the following exception. The silica binder solution was made up of a 50 weight percent solution (Nalco 2327 colloidal silica/DI $H_2O$) which was then diluted with water to 20% silica by weight. 202 grams of the Nalco 2327/DI $H_2O$ binder were required to wet 202 grams of the titanium dioxide power. The drying and grinding procedures were the same as described above.

Both titania-silica (Sample 1 and Sample 2) supports were then impregnated with 5 wt % rhodium as described below. A stock solution of rhodium (III) nitrate $[Rh(NO_3)_3 2H_2O]$ containing 0.0816 g Rh/cc was prepared. Approximately 34 grams of the support was placed in a 500 cc single neck glass round bottom flask, and 21.2 cc of the rhodium (III) nitrate stock solution was diluted and added to the flask. The flask was attached to a rotary evaporator and allowed to cold roll for 15 minutes. The water bath was heated to 60° to 80° C. and impregnation mixture allowed to roll to dryness, under vacuum. The flask was removed after 5-6 hours. The catalyst was scraped from the flask, placed in a crucible and dried @121° C. overnight in a drying oven. A 25% weight loss was observed. The dried catalyst was then passed through a 30 mesh screen to break up any lumps which formed during impregnation and drying. It was then muffle treated @370° C. for 2 hours. An additional 3% weight loss was observed.

EXAMPLE 2

Rhodium on Titania/Titania Sol 201 grams of titanium dioxide powder, e.g., Degussa P-25, having an average particle size of 15–40 nanometers and <1.5% moisture was added to a sigma blade mixer. Then, 171 grams of Nalco TX-2588, colloidal titanium oxide, ethylene glycol and alkylamine aqueous solution, containing 11.7% total solids as titanium dioxide was added to the powder. Mixing was completed in approximately 5 minutes or when a lumpy paste-like product was formed. The lumps were scraped from the mixer, placed in a drying tray and dried at 260° C. overnight. During the drying process there was approximately a 40% moisture loss with the dried lumps usually taking on a brown color. The dried lumps were then ground to −40+100 mesh particle size. In this case two pieces of grinding equipment were used: a 2 inch plate grinder, which broke up the larger lumps of titanium dioxide and a Thomas-Wiley Intermediate Mill, with a 20 mesh screen installed. Grinding was continued until all material passed through the 40 mesh screen. Only the particles which passed through the 40 mesh screen and stayed on the 100 mesh screen were saved and used as the support. Heat treatment on the size particles then followed to adjust the surface area and pore size distribution. The following table illustrates some of the properties of the support:

| Support | | Bulk Density g/cc | S.A. $m^2/g$ | Total Pore Vol. cc/g | Med. Pore Dia. Angstroms | Avg. Pore Dia. Angstroms |
|---|---|---|---|---|---|---|
| 2a | Dried @ 260° C. | 0.87 | 76.9 | .3885 | 240 | 185 |
| 2b | 500° C.-2 Hrs-100% Air | 0.91 | 62.4 | .4051 | 214 | 136 |

The heat treated support was then impregnated with 5% rhodium by weight using a rotary evaporator. A stock solution of rhodium (III) nitrate [Rh(NO$_3$)$_3$2H$_2$O] containing 0.08579 g Rh/cc was prepared. Approximately 34 grams of support was added to a 500 cc single neck glass round bottom flask, 20.2 cc of the rhodium (III) nitrate stock solution was diluted and added to the flask containing the support. The flask was attached to the rotary evaporator and allowed to cold roll for 15 minutes. The water bath was heated to 60° to 80° C. and the impregnated mixture was allowed to roll to dryness, under vacuum. The flask was removed after approximately 5-6 hours. The catalyst was scraped from the flask, placed in a crucible and dried @121° overnight. A 10-20% weight loss was observed in the drying step. The dried catalyst was then passed through a 30 mesh screen to break up any lumps which formed while impregnation and drying. The catalyst was then muffle treated @370° C.-2 hours. A 5% weight loss was observed during the muffle treatment. The activity test results for these two catalysts made from supports 2a and 2b are given in Table 1.

EXAMPLE 3

Rhodium Catalysts on Various Supports in Crude MDA Hydrogenation Reaction Process In a series of runs, a specified catalyst was charged to a 300 cc autoclave with 125 g of tetrahydrofuran (THF) and pretreated. The ruthenium cocatalyst, where added, was admixed with the rhodium catalyst as 5% by weight ruthenium on alumina. The sealed autoclave was purged with nitrogen followed with hydrogen and then pressurized to about 600 psig with hydrogen. The autoclave was then heated with agitation to 190° with addition of hydrogen as necessary to maintain a pressure of 850 psig at that temperature. After two hours, the autoclave was cooled to room temperature. After such reaction, it was believed the catalyst was fully reduced and suited for catalytic hydrogenation.

For catalytic hydrogenation of crude methylenedianiline ("MDA"), i.e., one containing oligomers and formamide derivatives of MDA, the THF was removed from the autoclave after pretreatment of the catalyst and replaced by the specified solution of crude MDA in THF substrate. If specified, lithium hydroxide was added as a 10% aqueous solution. The sealed autoclave was purged with nitrogen, followed with addition of hydrogen and then pressurized to about 600 psig with nitrogen. The autoclave was then heated with agitation to the specified reaction temperature and hydrogen was added from a ballast tank to maintain a pressure of 850 psig (a ballast tank was chosen of sufficient size and filled with hydrogen at sufficient pressure to provide all the hydrogen consumed in the reaction without dropping below 850 psig). The drop in pressure in the ballast tank provided a convenient method for observing the progress of the reaction. The reaction was considered complete hydrogen consumption stopped. After the reaction was complete, the autoclave was cooled to room temperature, vented and the product mixture removed. The product was analyzed by capillary GC using a method previously calibrated for the materials involved. The catalyst in some cases was reused (run uses) to determine its effectiveness in subsequent reactions and determine the extent of attrition. Table I notes reaction conditions and yield.

TABLE 1

| Run | Catalyst | Mole Ratio Rh/Ru | Catalyst Examples | Run Uses | Induction Time | Reaction time at 192° C. | Yield** | t.t. Isomer |
|---|---|---|---|---|---|---|---|---|
| A | 0.73 g Rh/TiO$_2$ | 4:1 | Commercially available TiO$_2$ catalyst | 1 | 35 min | 205 min | 96.4 | 16.9 |
|   | 0.18 g Ru/Al$_2$O$_3$ | | | 2 | | no attrition resistance - Run 2 not carried out | | |
| B | 0.73 g Rh/Al$_2$O$_3$ + | 4:1 | Commercial Al$_2$O$_3$ catalyst | 1 | 10 min | 190-220 min | 84-88% | 18-20% |
|   | 0.18 g Ru/Al$_2$O$_3$ | | | | | | | |
| C | 0.73 g Rh/TiO$_2$—SiO$_2$ + | 4:1 | Ex 1a | 1 | 05 min | 130 min | 76.1% | 20.6% |
|   | 0.18 g Ru/Al$_2$O$_3$ | | | 2 | 40 | 180 min | 83.9% | 18.2% |
|   | | | | 3 | 60 min | 240 min | 77.8% | 17.3% |
|   | | | | 4 | 80 min | 260 min | 78.4 | 19.6% |
| D | 0.73 g Rh/TiO$_2$—SiO$_2$ + | 4:1 | Ex 1b | 1 | 05 min | 110 min | 74.8 | 22.5 |
|   | 0.18 g Ru/Al$_2$O$_3$ | | | 2 | 25 min | 125 min | 79.4 | 16.7 |
| E | 0.73 g Rh/TiO$_2$—SiO$_2$ + | | Ex 1a | 1 | 10 min | 210 min (at 170° C.) | 81.5 | 15.1 |
|   | 0.18 g Ru/Al$_2$O$_3$ | | | | | | | |

TABLE 1-continued

| | | Hydrogenation of Crude-Methylenedianiline | | | | | |
|---|---|---|---|---|---|---|---|
| Run | Catalyst | Mole Ratio Rh/Ru | Catalyst Examples | Run Uses | Induction Time | Reaction time at 192° C. | Yield** | t.t. Isomer |
| F | 0.73 g Rh/TiO$_2$ + 0.18 g Ru/Al$_2$O$_3$ | 4:1 | Ex 2a | 1 | 0 min | 90 min | 82% | 24.6 |
| G | 0.73 g Rh/TiO$_2$ (heat treated + 0.18 g Ru/Al$_2$O$_3$ | 4:1 | Ex 2b | 1 | 0 min | 95 min | 87% | 22.5 |

*All catalysts were 5% by weight metal loading
**Calculated from PACM and half reduced MDA in reactor effluent versus MDA in feed The results in Table I show that the rhodium-ruthenium catalysts carried on the titania support chemically bonded with the silica sol (Runs C, D, and E) were superior in catalytic activity to the rhodium catalysts carried on alumina or and in attrition resistance to titania above (Runs A and B). Reaction time for the rhodium on silica support bonded with the titania sol was less than with other catalysts. This may be explained by Table 2 which showed that this catalyst had the lowest level of fine pores.

To explain differences in results achieved in Table 1, the catalysts of Examples 1 and 2 were composed to a commercial catalyst of rhodium on alumina support (same level of rhodium) to determine surface area and pore size. Table 2 shows the major difference in pore size distribution between the Example 1 and 2 titania supported catalysts vis-a-vis or commercial rhodium-alumina catalyst. The commercial rhodium-alumina catalyst had only 16% of its pores in the desired greater than 100A° range. The titania bound by silica sol had 47% of its pores in the desired range while titania bound by titania sol had 66% of its pores greater than 100° A.

TABLE 2

Impact of Small Pore Surface Area on Efficiency of Metal Use

| Catalyst | Percentage of Pores >100A° | Surface Area (BET) Total m$^2$/g | <100A (%) m$^2$/g |
|---|---|---|---|
| Commercial Rh/alumina | 16 | 100 | 16 |
| Example 1 | 47 | 89.3 | 42 |
| Example 2 | 66 | 75.2 | 49.6 |

The vast majority (84%) of the surface area of the alumina support is in pores of less than 100A in diameter. The metal deposited in these small pores is believed to contribute little to the catalyst activity. The titania agglomerated with a silica sol had only 53% of its surface area in these small pores thus much more of the rhodium is available to contribute to activity. The titania agglomerated with the titania sol had only 34% of its surface area in these small pores.

EXAMPLE 4

Rhodium on Silica

Preparation of a 5% rhodium catalyst was carried out in the following manner. 30 grams of hollow silica spheres, Philadelphia Quartz Q-Cel 600, were contacted with 155 cc of a solution containing 1.58 grams of rhodium. This mixture was placed in a rotary evaporator, heated as before and evacuated to dryness. The solids were removed and dried overnight at 121° C. 33.6 grams of catalyst were recovered.

A 300 cc autoclave was charged with 1.5 weight % of the catalyst and 125 g of THF. Following purging and pressurizing with hydrogen, the autoclave was heated to 192° C. at 850 psi total pressure for 2 hours. It was then cooled, vented and the THF was removed under nitrogen. 125 g of 42% crude MDA in THF was added to the autoclave. Following purging and pressurizing with hydrogen, the autoclave was heated to 192° C. A total pressure of 850 psi was maintained from à ballast tank. The separation was done using Whatman #1 filter paper. The reaction product was analyzed and the results are summarized in Table 3.

TABLE 3

Activity Results of the Hydrogenation of Crude MDA Using Rh on SiO$_2$

| Catalyst | Induction Period | Reaction Time at 192° C. (min) | Conversion % | Yield to PACM | Yield to ½ PACM | t,t Isomer % |
|---|---|---|---|---|---|---|
| Rh/SiO$_2$ | 200 | 240 | 10.5 | 0.9 | 20.1 | 23.4 |

This example shows that there is essentially no reaction and the rhodium silica catalyst was ineffective for hydrogenating crude MDA when rhodium is supported on silica alone, although the catalyst system was reasonably easy to separate from the reaction mixture. It is generally known that a rhodium catalyst alone is ineffective for hydrogenating crude MDA at low pressure, e.g., 850 psig.

EXAMPLE 5

Rh on Titania Coated Silica

Preparation of a 5% rhodium on titania coated silica catalyst. The U.S. Standard mesh sieve silica support (Houdry HSC-534) was ground and screened through a 40 and on 100 mesh. The coated support is then prepared by treating 30 grams of the prescreened silica support with 28.5 g of titanium isopropoxide in hexane solution. The solvent is removed by rotary evaporation and the resulting solids dried at 60° C. and muffle heat treated at 550° C. 27.1 grams of the support were contacted with 100 cc of a solution containing 1.43 grams of rhodium. This mixture was placed in a rotary evaporator, heated and evacuated to dryness. The solids were removed and dried overnight at 121° C. They were given an additional muffle treatment at 370° C. 28.2 grams of catalyst were recovered.

A 300 cc autoclave was charged 1.5 weight % of the catalyst and 1255 g of THF. Following purging and pressurizing with hydrogen, the autoclave was heated to 192° C. at 850 psi total pressure for 2 hours. It was then cooled, vented and the THF was removed under nitrogen. 125 g of 42% crude MDA in THF was added to the autoclave. Following purging and pressurizing with hydrogen, the autoclave was heated to 192° C. A total pressure of 850 psi was maintained from a ballast tank. The catalyst was readily recovered from the reaction mixture with ease. The results are summarized in Table 4.

TABLE 4

| | Activity Results of the Hydrogenation of Crude MDA | | | | |
|---|---|---|---|---|---|
| Catalyst | Induction Period (min) | Reaction Time at 192° C. (min) | Conversion % | Yield to PACM | Yield to ½ PACM | t,t Isomer % |
| Rh/SiO₂/TiO₂ | 0 | 70 | 99 | 64.0 | 1.5 | 20.7 |

This example demonstrates the effectiveness of supporting rhodium on a titania surface bonded to a silica substrate. Further, the catalyst showed more resistance to attrition than commercial titania or alumina supported catalyst. The hydrogen uptake rate is extremely high and activity is equivalent to a rhodium catalyst supported on titania.

EXAMPLE 6

Hydrogenation Using Rhodium on Zirconia/Silica Support

Preparation of 2.5% rhodium on zirconia/silica support. The support is prepared by treating contacting solutions of zirconia nitrate (162 g in 300 cc) and N-Brand sodium silicate (277 g in 350 cc) in a mixing/spray head. The resulting thick, white precipitate (pH=6.85) was filtered, was 5× with hot, DI water and dried overnight at 95° C. This composition was selected to produce a neutral precipitate, but may be varied to change the support acidity. This will modify the catalytic performance of the final product. The solids were crushed and screened through 40 and on 200 mesh. 37.8 g of these solids were contacted with 100 cc of a solution containing 0.97 grams of rhodium. This mixture was placed in a rotary evaporator, heated and evacuated to dryness. The solids were removed and dried overnight at 250° F. The solids were given an additional muffle treatment at 700° F. 35 grams of catalyst were recovered.

A 300 cc autoclave was charged with 3.0 weight % of the catalyst and 125 g of THF. Following purging and pressurizing with hydrogen, the autoclave was heated to 195° C. at 850 psi total pressure for 2 hours. It was then cooled, vented and the RHF was removed under nitrogen. 125 g of 42% crude MDA in THF was added to the autoclave. Following purging and pressurizing with hydrogen, the autoclave was heated to 192° C. A total pressure of 850 psi was maintained from a ballast tank. The results are summarized in Table 5.

TABLE 5

| | Activity Results of the Hydrogenation of Crude MDA | | | | |
|---|---|---|---|---|---|
| Catalyst | Induction Period (min) | Reaction Time at 192° C. (min) | Conversion % | Yield to PACM | Yield to ½ PACM | t,t Isomer % |
| Rh/SiO₂/ZrO₂ | 0 | 150 | 100 | 62.5 | 0 | 22.9 |

This example demonstrates the effectiveness of the mixed oxide composition. The hydrogen uptake rate is very good. This support preparation technique may also be used to prepare supports of varying acidity to influence the catalytic performance of the product. The catalyst was readily separated from the reaction mixture.

EXAMPLE 7

Hydrogenation on Rhodium on Zirconia-Alumina Support

Preparation of a 2.5% rhodium on zirconia/alumina support. The support is prepared by treating contacting solutions of zirconium oxy nitrate (296 g in 250 cc) and LaRoche SOAL 235, sodium aluminate (135 g in 250 cc) in a mixing/spray head. The resulting thick, white precipitate (pH=7.3) was filtered, washed 5× with DI water and dried overnight at 95° C. in air. This composition was selected to produce a neutral precipitate but may be varied to change the support acidity. The solids were crushed and screened through 40 and on 200 mesh. 33.2 g of these solids were contacted with 155 cc of a solution containing 0.85 grams of rhodium. This mixture was placed in a rotary evaporator, heated and evacuated to dryness. The solids were removed and dried overnight at 250° F. They were then given an additional 700° F. muffle treatment. 23.8 grams of catalyst were recovered.

A 300 cc autoclave was charged with the 3.0 weight % catalyst and 125 g of THF. Following purging and pressurizing with hydrogen, the autoclave was vented and the THF was removed under nitrogen. 125 g of 42% crude MDA in THF was added to the autoclave. Following purging and pressurizing with hydrogen, the autoclave was heated to 192° C. A total pressure of 850 psi was maintained from a ballast tank. The results are summarized in Table 6.

TABLE 6

| | Activity Results of the Hydrogenation of Crude MDA | | | | |
|---|---|---|---|---|---|
| Catalyst | Induction Period (min) | Reaction Time at 192° C. (min) | Conversion % | Yield to PACM | Yield to ½ PACM | t,t Isomer % |
| Rh/Al₂O₃/ZrO₂ | 10 | 260 | 63 | 39.5 | 46.3 | 18.9 |

This example demonstrates the effectiveness of the mixed oxide composition. The product yield is good and the deamination level is low. This support preparation technique may also be used to prepare supports of varying acidity to influence the performance of the product. However, the catalyst did not readily separate from the reaction products.

What is claimed is:

1. In a process for the catalytic hydrogenation of aromatic amines to their ring, hydrogenated counterparts, by contacting the aromatic amine with hydrogen in the presence of a rhodium catalyst, the improvement which comprises effecting said hydrogenation in the presence of a catalyst comprising rhodium on a support selected from the group consisting of titania chemically bonded with silica, optionally via a sol, and titania chemically bonded with titania via a sol.

2. The process of claim 1 wherein the aromatic amine is represented by the formulas:

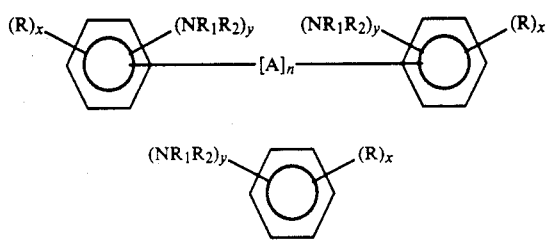

wherein R is hydrogen or $C_{1-6}$ aliphatic, R1 and R2 are hydrogen or $C_{1-6}$ aliphatic, A is $C_{1-4}$ alkylene, NH or

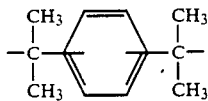

n is 0-2, x is 1-3 and y is 0 to 2 except the sum of the y groups in Formula I excluding A may be 1.

3. The process of claim 2 wherein said aromatic amine is represented by formula I.

4. The process of claim 3 wherein the amount of rhodium on the titania support ranges from about 1 to 25 parts by weight, as metal, per 100 parts titania.

5. The process of claim 4 wherein ruthenium is added as a co-catalyst to the hydrogenation process and the ratio of rhodium to ruthenium, as metal, is from about 1-12 weight parts rhodium per 1 weight part ruthenium.

6. The process of claim 5 wherein the catalyst is present in an amount from about 0.1 to 10% by weight of the aromatic amine.

7. The process of claim 6 wherein R is hydrogen, methyl, ethyl or tert-butyl.

8. The process of claim 7 wherein each y is 1.

9. The process of claim 7 wherein R1 and R2 are hydrogen.

10. The process of claim 8 wherein the support comprises from about 10 to 60 parts in the support by weight silica or titania derived from a silica or titania sol per 100 parts titania.

11. The process of claim 9 wherein the support is titania bonded with a titania sol.

12. The process of claim 9 wherein n is 0.

13. The process of claim 10 wherein A is $CH_2$ and n is 1.

14. The process of claim 11 wherein the temperature of the reaction is within the range from about 100° to 220° C.

15. The process of claim 10 wherein the reaction is carried out in the presence of an organic solvent.

16. The process of claim 5 wherein the catalyst system comprises rhodium and ruthenium and the amount of rhodium is from 4 to 8 weight parts/weight part ruthenium, the aromatic amine is methylenedianiline and the amount of catalyst based on methylenedianiline is from 0.5 to 5% by weight.

17. The process of claim 6 wherein said titania support is titania bonded to a silica substrate.

18. The process of claim 1 wherein said aromatic amine is represented by formula II.

19. The process of claim 18 wherein the catalyst is present in an amount from about 0.5 to 5% by weight of the aromatic amine.

20. The process of claim 19 wherein the rhodium ranges from about 1 to about 25 parts by weight, as metal, per 100 weight parts titania support bonded to silica or titania sol.

21. The process of claim 20 wherein R1 and R2 are hydrogen.

22. The process of claim 21 wherein R is methyl, ethyl, or tert-butyl and x is 1 or 2.

23. The process of claim 21 wherein y is 1.

24. The process of claim 23 wherein the titania support is bonded to titania via a titania sol.

25. The process of claim 24 wherein the temperature of the reaction is within the range from about 130° to 220° C.

26. The process of claim 24 wherein the reaction is carried out in the presence of an organic solvent.

27. The process of claim 21 wherein ruthenium is added as a co-catalyst to the hydrogenation process and the ratio of rhodium to ruthenium, as metal, is from about 1-12 weight parts rhodium per weight part ruthenium.

* * * * *